(12) United States Patent
Alessandrini

(10) Patent No.: US 8,237,008 B1
(45) Date of Patent: Aug. 7, 2012

(54) PARTIALLY RIGID BANDAGE APPARATUS

(76) Inventor: Jose A. Alessandrini, Miami, FL (US)

( * ) Notice: Subject to any disclaimer, the term of this patent is extended or adjusted under 35 U.S.C. 154(b) by 277 days.

(21) Appl. No.: 12/786,144

(22) Filed: May 24, 2010

(51) Int. Cl.
*A61F 13/00* (2006.01)

(52) U.S. Cl. ........ 602/42; 602/41; 602/58; 602/60; 602/61; 602/62; 602/63; 128/888; 128/889

(58) Field of Classification Search .......... 602/41–59; 604/174, 178, 179, 198; 128/888, 889
See application file for complete search history.

(56) References Cited

U.S. PATENT DOCUMENTS

| | | | | |
|---|---|---|---|---|
| 260,561 A * | 7/1882 | French | ............. | 128/888 |
| 2,367,690 A * | 1/1945 | Purdy | ............. | 128/888 |
| 2,785,677 A * | 3/1957 | Stumpf | ............. | 602/59 |
| 3,234,941 A * | 2/1966 | Tucker | ............. | 128/888 |
| 4,926,848 A | 5/1990 | Shimkus et al. | | |
| 5,068,763 A * | 11/1991 | Brown et al. | ............. | 361/659 |
| 5,580,346 A * | 12/1996 | Spier | ............. | 602/42 |
| 5,702,356 A * | 12/1997 | Hathman | ............. | 602/41 |
| 6,107,536 A | 8/2000 | Dadinis | | |
| 6,506,175 B1 | 1/2003 | Goldstein | | |
| D485,908 S | 1/2004 | Sachi | | |
| 7,265,256 B2 * | 9/2007 | Artenstein | ............. | 602/42 |
| 7,605,299 B2 * | 10/2009 | Zocher | ............. | 602/58 |

* cited by examiner

*Primary Examiner* — Kim M Lewis

(57) ABSTRACT

The partially rigid bandage apparatus has a band having a first end spaced apart from a second end, a pair of identical spaced apart sides, a top and a bottom, a fastening device releasably fastening the first end to the second end, an opening disposed within about a center of the band, a rigid bubble disposed atop and extended above the opening, the rigid bubble affixed to a border of the opening via an accordion membrane that allows distal and proximal movement of the bubble with regard to the band, such that a selected body sight is protected from abrasion and impact, the apparatus repeatedly reusable.

1 Claim, 4 Drawing Sheets

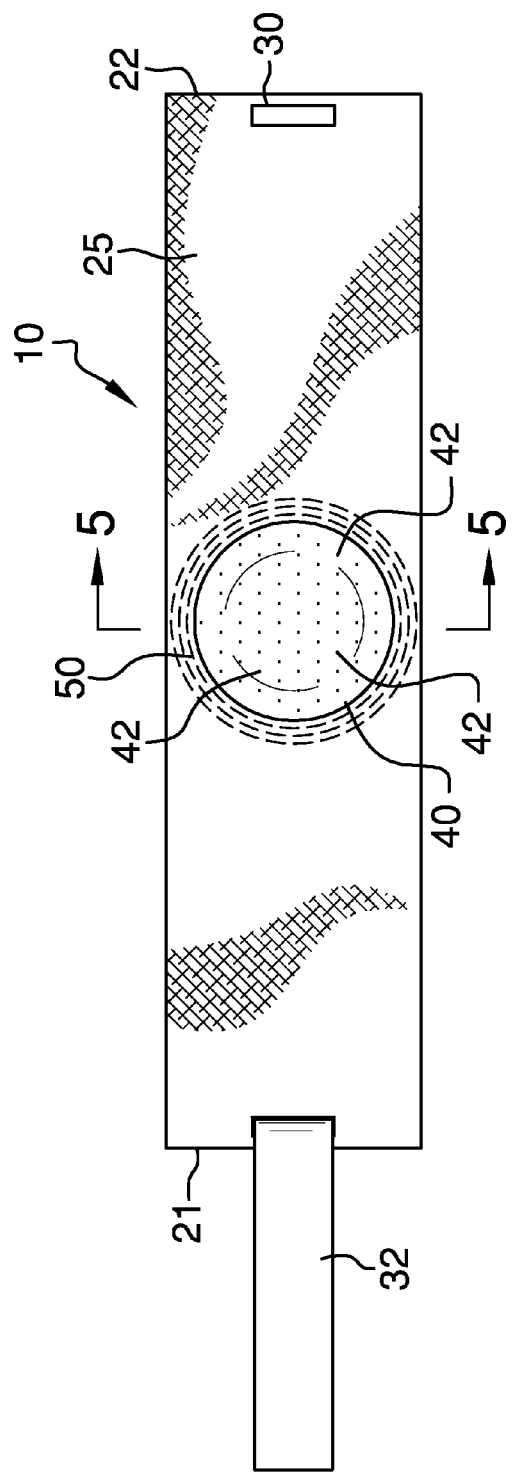
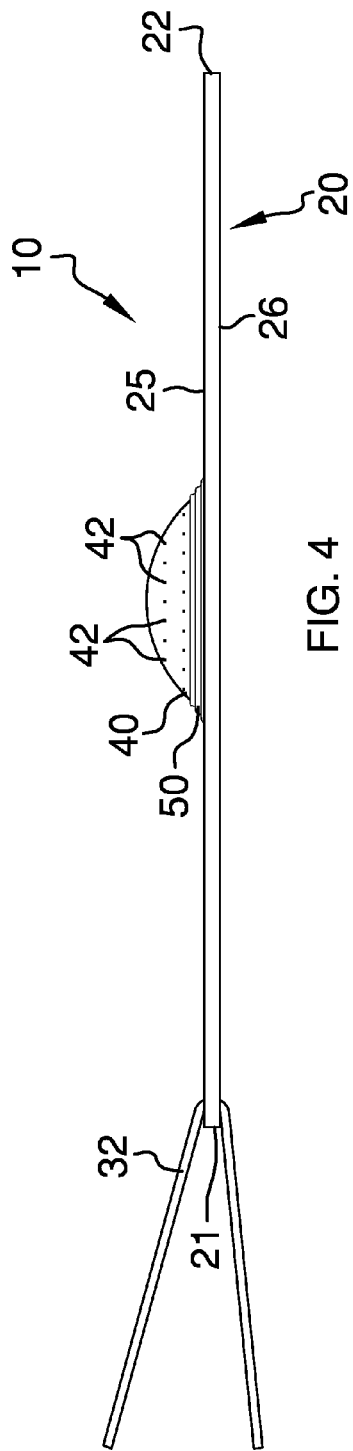
FIG. 3
FIG. 4

PARTIALLY RIGID BANDAGE APPARATUS

BACKGROUND OF THE INVENTION

Even though a variety of bandages are available in premade form, several needs remained unfulfilled prior to the present apparatus. For example, bandages that stick to skin also stick to hair and can be quite undesirable, hard to remove, and usually leave residue. Also, sticky bandages are seldom sized to accommodate many injury sites. Bandages that don't stick require various tapes and the like to properly locate on a site that needs covering. Many bandages do not breathe. The present apparatus provides solutions to these problems and more. The apparatus protects most any injury or site that needs protection, and does so with partially rigid protection so that the site is not invaded by being bumped or abraded. The apparatus does not require adhesives and is fully adjustable for fit.

FIELD OF THE INVENTION

The partially rigid bandage apparatus relates to bandages.

SUMMARY OF THE INVENTION

The general purpose of the partially rigid bandage apparatus, described subsequently in greater detail, is to provide a partially rigid bandage apparatus which has many novel features that result in an improved partially rigid bandage apparatus which is not anticipated, rendered obvious, suggested, or even implied by prior art, either alone or in combination thereof.

To attain this, the partially rigid bandage apparatus may provide a flexible band or an elastic band. The apparatus may fasten the open ended band with any appropriate fastener device, including hook and loop. The band may be fastened by a flexible attachment strip or even an elastic attachment strip, selective or permanently fastened to ends or the band. Of criticality is that the band comprises an opening over which is positioned a bubble. The bubble and opening may be of any shape or size, and, therefore, the band may be of virtually any appropriate width. Importantly, the bubble is rigid and therefore prevents any incursion of an injury site or any site that requires protection. The bubble may be transparent, translucent, or opaque.

In the ideal embodiment, the vertical step extended downwardly from the bubble's exterior perimeter further guards a protected site by abutting against the band and preventing the bubble from potential collapse into the site. Perforations may be critical in allowing a protected site to breath. Such breathing may be especially important in cases of burns and abrasions, for example. Sufficient protection of stitches is also achieved by the apparatus, as is any agitation that might otherwise be caused by clothing.

The apparatus may be provided in various sizes and shapes not illustrated, so that any number of bodily sites may be accommodated. The apparatus is easily adjustably fitted and does not use adhesives. Therefore, no skin or hair irritation occurs and no adhesive residue remains. Of further important consideration is that the apparatus may be used with or without other site protection means, such as medicated bandages, for example, and does not interfere with same but rather provides protection. A vital feature is that the apparatus may be used repeatedly, rather than discarded as is the case with most bodily site protection devices.

Thus has been broadly outlined the more important features of the improved partially rigid bandage apparatus so that the detailed description thereof that follows may be better understood and in order that the present contribution to the art may be better appreciated.

An object of the partially rigid bandage apparatus is to fully protect a needed site.

Another object of the partially rigid bandage apparatus is to negate the use of adhesives.

A further object of the partially rigid bandage apparatus is to be adjustably applied.

An added object of the partially rigid bandage apparatus is to be easily applied and removed, repeatedly.

And, an object of the partially rigid bandage apparatus is to allow a protected site to breathe.

These together with additional objects, features and advantages of the improved partially rigid bandage apparatus will be readily apparent to those of ordinary skill in the art upon reading the following detailed description of presently preferred, but nonetheless illustrative, embodiments of the improved partially rigid bandage apparatus when taken in conjunction with the accompanying drawings.

In this respect, before explaining the current embodiments of the improved partially rigid bandage apparatus in detail, it is to be understood that the partially rigid bandage apparatus is not limited in its application to the details of construction and arrangements of the components set forth in the following description or illustration. Those skilled in the art will appreciate that the concept of this disclosure may be readily utilized as a basis for the design of other structures, methods, and systems for carrying out the several purposes of the improved partially rigid bandage apparatus. It is therefore important that the claims be regarded as including such equivalent constructions insofar as they do not depart from the spirit and scope of the partially rigid bandage apparatus. It is also to be understood that the phraseology and terminology employed herein are for purposes of description and should not be regarded as limiting.

BRIEF DESCRIPTION OF THE DRAWINGS

FIG. 3 is a top plan view.
FIG. 4 is a lateral elevation view.

DETAILED DESCRIPTION OF THE DRAWINGS

With reference now to the drawings, and in particular FIGS. 1 through 5 thereof, the principles and concepts of the partially rigid bandage apparatus generally designated by the reference number 10 will be described.

Figure 2:
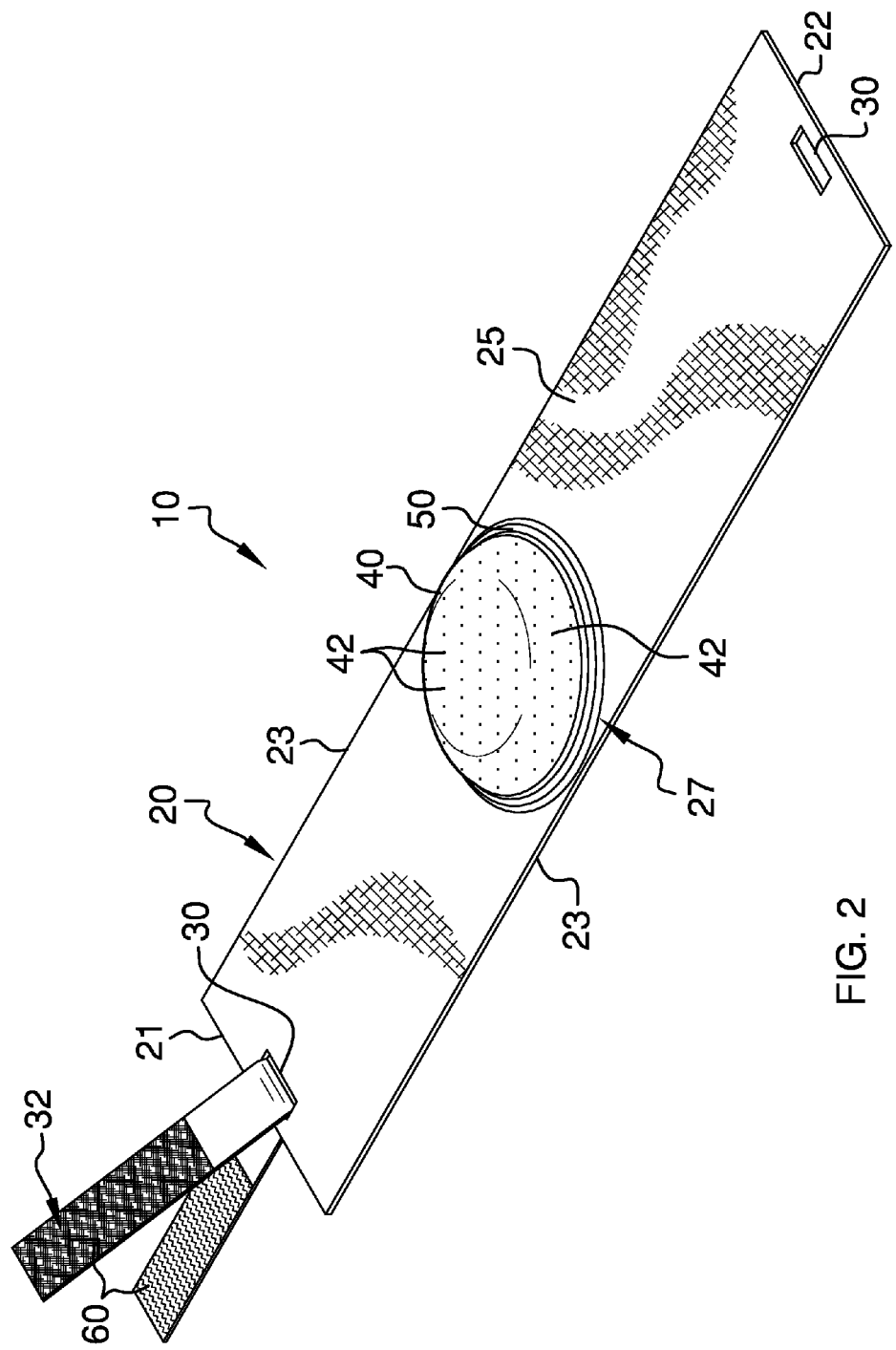
FIG. 2 is a top perspective view.

Referring to FIGS. 2 and 3, the apparatus 10 partially comprises an elastic band 20 having a first end 21 spaced apart from a second end 22, and a pair of identical spaced apart sides 23.

Referring to FIG. 4, the apparatus 10 further partially comprises a top 25 and a bottom 26.

Referring to FIG. 2, a slot 30 is disposed within each end of the band 20. Each slot 30 is parallel with the ends.

Referring again to FIGS. 2 and 4, a flexible attachment strip 32 is removably disposed within each slot 30. Hook and loop fastener 60 is disposed on the attachment strip 32 and selectively fastens the attachment strip 32 to itself.

Figure 5:
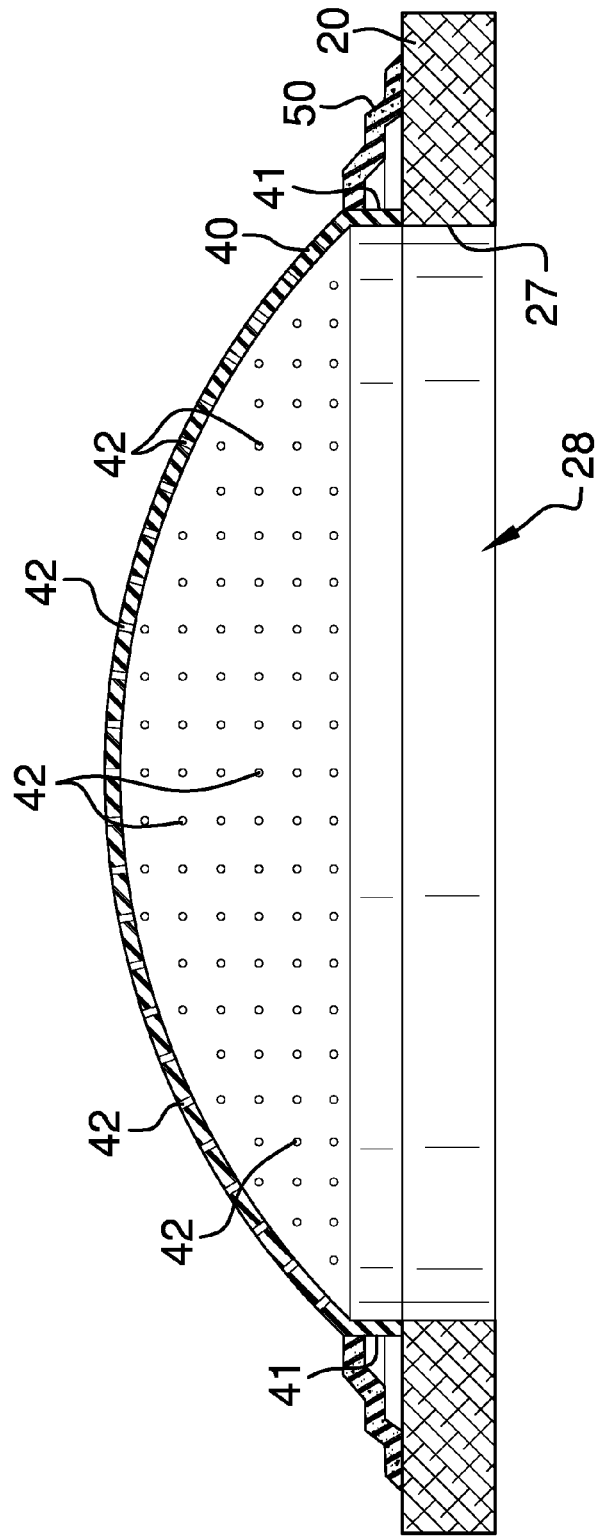
FIG. 5 is a partial cross sectional view of FIG. 3, taken along the line 5-5.

Referring to FIG. 5, an opening 28 is disposed within about a center of the band 20. The border 27 is disposed within the band 20 around the opening 28. The accordion membrane 50 is affixed to the band 20 top 25 immediately exterior to the border 27. The rigid bubble 40 is disposed atop and extended above the opening 28. The plurality of spaced apart perforations 42 is disposed throughout the bubble 40. The vertical step 41 is disposed downwardly around and is affixed to the bubble 40. The vertical step 41 is affixed to the accordion membrane 50. The vertical step 41 abuts the band 20 top 25 immediately exterior to the border 27. The accordion membrane allows the bubble 40 to flex outwardly and inwardly from the band 20 top 25. The vertical step 41 prevents the bubble from any undesired compression of a user's protected site.

Figure 1:
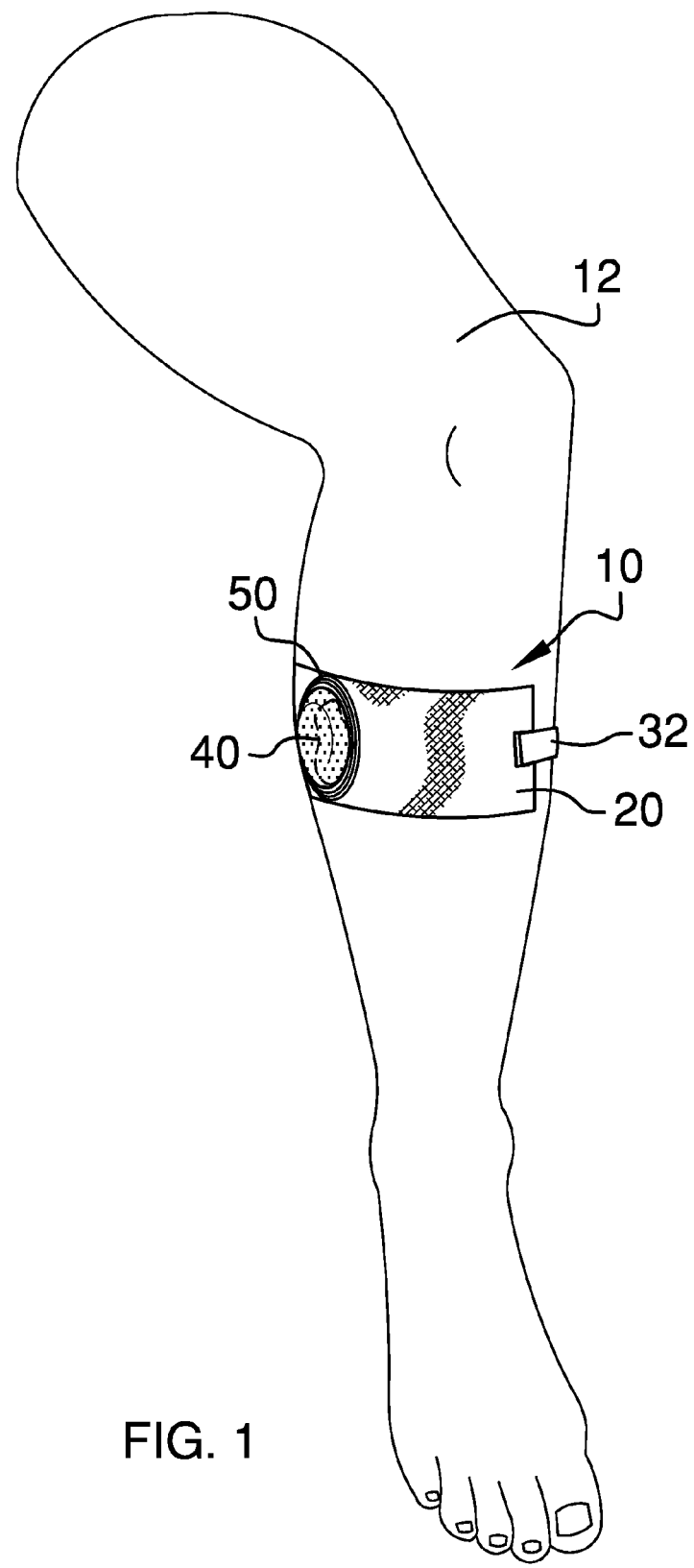
FIG. 1 is a perspective view of the apparatus in use on a leg.

Referring to FIG. 1, the apparatus 10 is fitted around a user's leg 12 to cover a site deserving protection. The elastic band 20 retains the apparatus 10 fitted location on the leg 12. The attachment strip 32 is disposed through the slots 30 of the band 20 and hooked to itself via the hook and loop 60.

With respect to the above description then, it is to be realized that the optimum dimensional relationships for the parts of the partially rigid bandage apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the partially rigid bandage apparatus.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the partially rigid bandage apparatus may be used.

Therefore, the foregoing is considered as illustrative only of the principles of the partially rigid bandage apparatus. Further, since numerous modifications and changes will readily occur to those skilled in the art, it is not desired to limit the partially rigid bandage apparatus to the exact construction and operation shown and described, and accordingly, all suitable modifications and equivalents may be resorted to, falling within the scope of the partially rigid bandage apparatus.

What is claimed is:

1. A partially rigid bandage apparatus comprising, in combination:
    an elastic band having a first end spaced apart from a second end, a pair of identical spaced apart sides, a top and a bottom;
    a slot disposed within each end of the band, each slot parallel with the ends;
    a flexible attachment strip removably disposed within the slots;
    a hook and loop fastener disposed on the attachment strip and selectively fastening the attachment strip to itself;
    an opening disposed within about a center of the band;
    a border disposed within the top around the opening;
    an accordion membrane affixed to the band top immediately exterior to the border;
    a rigid bubble disposed atop and extended above the opening;
    a plurality of spaced apart perforations disposed throughout the bubble;
    a vertical step disposed downwardly around and affixed to the bubble, the vertical step affixed to the accordion membrane, the vertical step abutting the band top immediately exterior to the border.

* * * * *